United States Patent [19]

Swanson

[11] Patent Number: 4,936,854
[45] Date of Patent: Jun. 26, 1990

[54] SEMI-CONSTRAINED WRIST IMPLANT

[76] Inventor: Alfred B. Swanson, 2945 Bonnell, SE., Grand Rapids, Mich. 49506

[21] Appl. No.: 288,461

[22] Filed: Dec. 22, 1988

[51] Int. Cl.$^5$ .............................................. A61F 2/42
[52] U.S. Cl. ........................................ 623/21; 623/18
[58] Field of Search .............................. 623/18, 21, 16

[56] References Cited

U.S. PATENT DOCUMENTS

| | | | |
|---|---|---|---|
| 3,879,767 | 4/1975 | Stubstad | 623/18 |
| 3,987,500 | 10/1976 | Schlein | 623/18 |
| 4,131,957 | 1/1979 | Bokros | 623/18 |
| 4,645,505 | 2/1987 | Swanson | 623/21 |
| 4,784,661 | 11/1988 | Beckenbaugh et al. | 623/21 |

Primary Examiner—Alan W. Cannon
Attorney, Agent, or Firm—Price, Heneveld, Cooper, DeWitt & Litton

[57] ABSTRACT

A wrist implant for stabilizing the proximal carpal row and prevent ulnar migration thereof while permitting movement at the radiocarpal joint includes a body having a generally planar, proximal surface which has a teardrop shape. The body further defines a generally triangular or wedge-shaped dorsal surface which is joined to a curved medial surface. The body defines a smooth recess including a lunate surface. The recess is configured to receive the carpal row lunate bone and is open distally and palmarly. The implant further includes a proximal stem which extends perpendicular to the proximal surface. The implant is adapted to be positioned at the distal end of the radius with the stem inserted into the intramedullary canal of the radius bone. The implant constrains the proximal row of the carpal bones, stabilizing the joint and preventing ulnar migration of the wrist bones.

6 Claims, 3 Drawing Sheets

SEMI-CONSTRAINED WRIST IMPLANT

This application is related to U.S. Pat. No. 4,645,505, entitled WRIST IMPLANT and which issued on Feb. 24, 1987 to the present inventor.

BACKGROUND OF THE INVENTION

The present invention relates to arthroplastic reconstruction of the human joints and more particularly to implant arthroplasty of the wrist joint In recent years, various implants have been successfully employed for the restoration of the joints of the hand and wrist affected with rheumatoid arthritis and similar conditions. Aseptic necrosis and/or arthritis of the carpal bones, either primary or secondary to trauma, is a frequent cause of disability of the wrist. Surgical treatment of conditions of the wrist have included intercarpal fusion, wrist fusion, local resection, proximal row carpectomy, bone grafting, radial styloidectomy, radial shortening or ulnar lengthening and soft tissue interposition arthroplasty.

Rheumatoid arthritis may affect the soft tissues and the joints of the wrist, including the radiocarpal, intercarpal and radioulnar joints. The disease may result in loosening of the ligaments and erosive changes in the bones. This disturbs the multiple link system of the wrist joint. In severe cases, the wrist may become completely dislocated. Ulnar displacement of the proximal carpal row may result from loosening of the ligaments on the radial aspect of the joint. Radial deviation of the hand on the forearm may then result. Subluxation of the distal radioulnar joint associated with such deviation causes a loss of stability on the ulnar aspect of the wrist.

Wrist implant arthroplasty has been employed when instability of the wrist is caused by subluxation or dislocation of the radiocarpal joint. A double stem implant has been used with one stem inserted into the intramedullary canal of the radius and the other stem inserted in a channel reamed through the remnant of the capitate bone and the third metacarpal. In addition, an intramedullary stemmed, cuffed implant may be used to cap the resected distal ulna to preserve the anatomic relationships and physiology of the distal radioulnar joint following ulnar head resection.

The aforementioned U.S. Pat. No. 4,645,505 overcomes many problems heretofore experienced with wrist implant arthroplasty. The implant disclosed therein defines a recess dimensioned to receive a portion of the carpal row and prevent ulnar migration of the row and wrist dislocation. The implant has a dorsal sidewall and a palmar sidewall and is symmetrical about a longitudinal centerline. The implant locks the lunate and prevents ulnar migration of the carpal tunnel row. The implant, however, shifts extension and flexion movements to the midcarpal joint. While reducing pain and stabilizing the wrist, movement is limited.

A need exists for an implant for the wrist which stabilizes the radiocarpal joint and proximal carpal row but which does not shift movement to the midcarpal joint.

SUMMARY OF THE INVENTION

In accordance with the present invention, a relatively rigid wrist implant is provided for stabilizing the proximal carpal row to restrict or prevent ulnar translation of the carpal bones while permitting close to normal flexion and extension. Essentially, the implant includes a body which defines a proximal surface. A dorsal sidewall extends perpendicular to the proximal surface. The sidewall joins to an end wall. The end wall and sidewall define a carpal recess dimensioned to receive a portion of the carpal row and prevent ulnar migration of the row. The recess opens distally and in a palmar direction to permit extension and flexion of the wrist.

In narrower aspects of the invention, the recess is undercut into the end wall and is dimensioned to receive the lunate bone of the proximal carpal row. The body is generally wedge-shaped in dorsal plan, and the proximal surface has a generally teardrop shape. The body further defines a proximal intramedullary stem dimensioned to be inserted into the intramedullary canal of the radius bone. In the preferred form, the implant is fabricated as a one-piece member from a medical grade titanium alloy or a medical grade superalloy based on nickel and/or cobalt and to which chromium is added. The implant constrains the carpal bones, stabilizes the wrist joint and yet permits wrist motion to occur at the radiocarpal joint. In addition, the implant may provide a distal buttress and surface for an ulnar head implant or cap.

DETAILED DESCRIPTION OF THE PREFERRED EMBODIMENT

Figure 1:
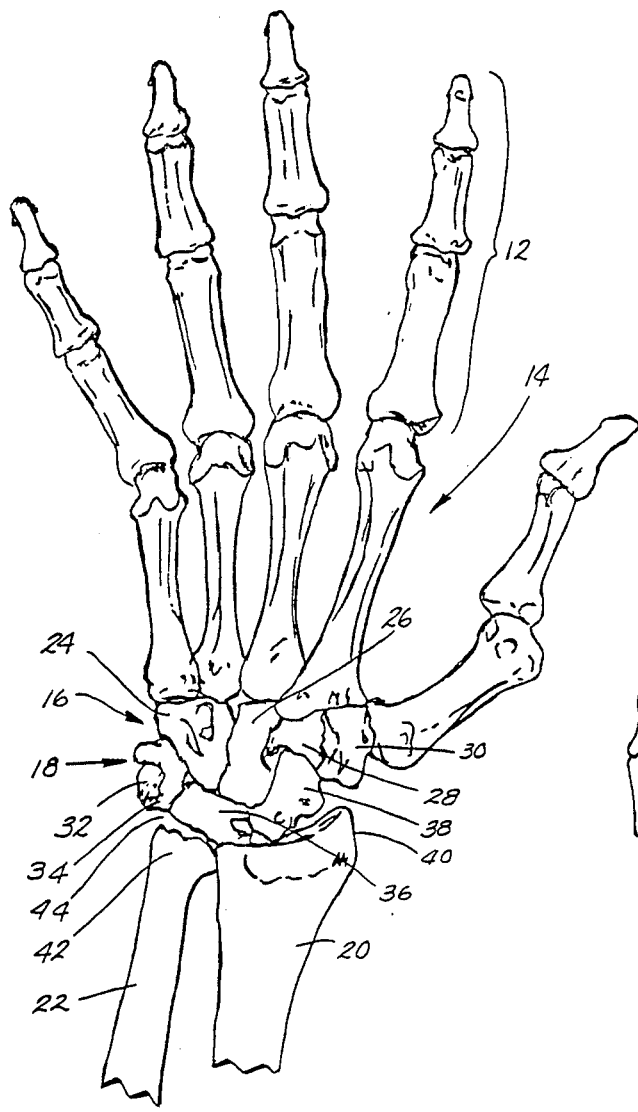
FIG. 1 is a fragmentary, dorsal view of the hand, wrist and distal portions of the ulna and radius.

With reference to the drawings, FIG. 1 illustrates a dorsal view of a hand and wrist. The hand includes phalanges 12, metacarpals 14, a distal carpal row 16 and a proximal carpal row 18. The proximal carpal row is adjacent the radius 20 and the ulna 22. The distal carpal row 16 includes the hamate 24, the capitate 26, the trapezoid 28 and the trapezium 30. The proximal carpal row includes the pisiform 32, the triquetrum 34, the lunate 36 and the scaphoid 38. The distal end of the radius 20 includes a styloid process 40. The distal end or head 42 of the ulna includes a styloid process 44. In the wrist illustrated in FIG. 1, the proximal carpal row 18 has migrated medially towards the ulna 22. The radiocarpal joint between the radius and the scaphoid and lunate has been affected and severe wrist impairment is present. Ulnar displacement of the proximal carpal row is typically the result of rheumatoid arthritis.

Figure 2:
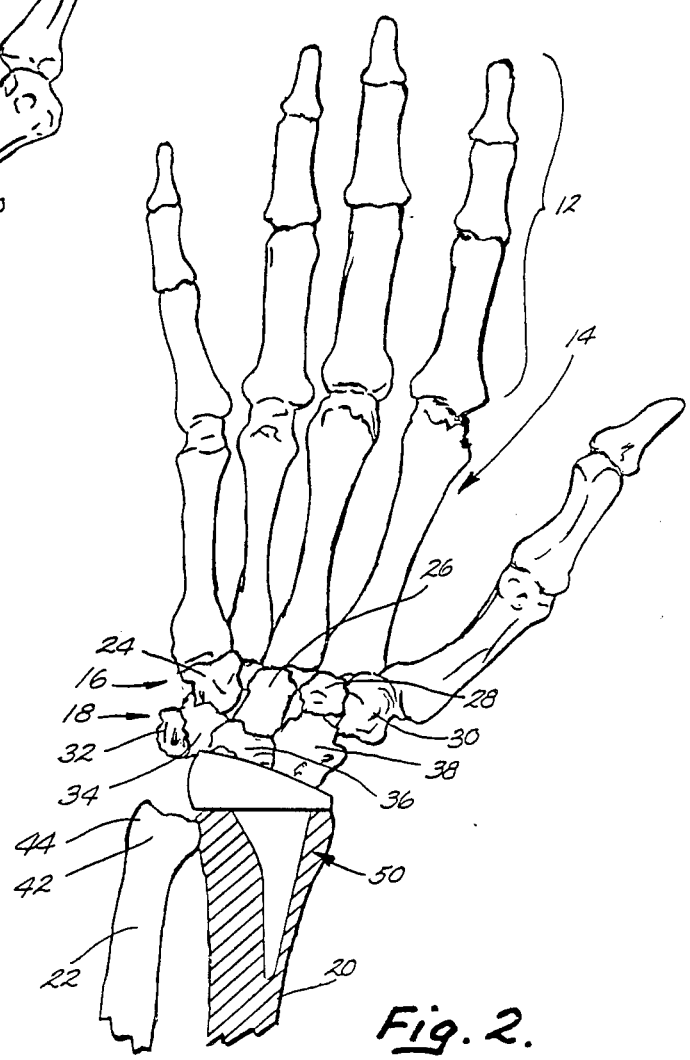
FIG. 2 is a fragmentary, dorsal view of the hand, wrist and distal portions of the radius and ulna showing a wrist implant in accordance with the present invention.
Figure 3:
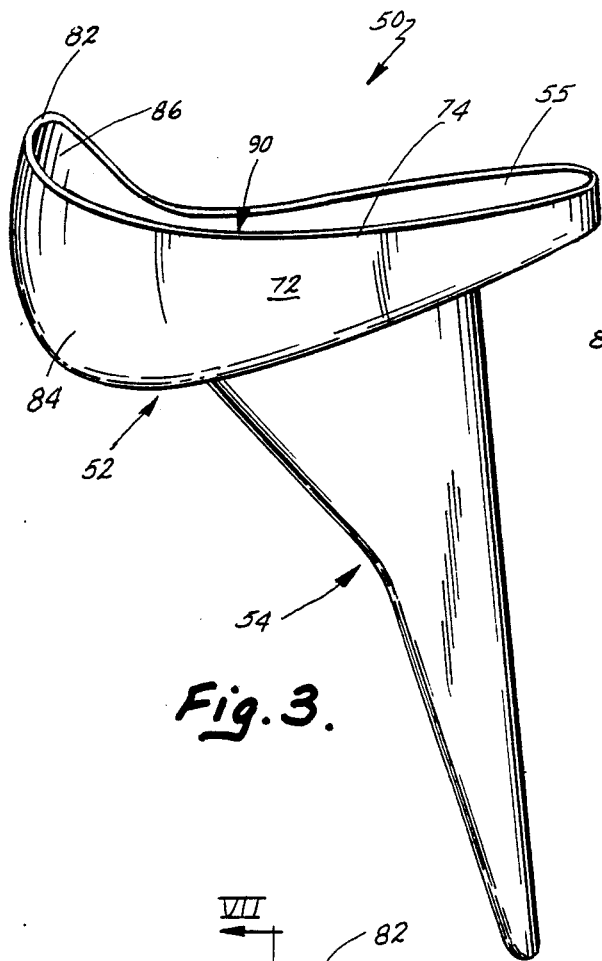
FIG. 3 is a perspective view of the implant.

In accordance with the present invention, a wrist implant generally designated 50 in FIG. 2 is provided to stabilize the proximal carpal row and constrain or prevent movement or ulnar displacement of the proximal row. Implant 50 is an improvement over that disclosed in aforementioned U.S. Pat. No. 4,645,505. As illustrated in FIG. 2, implant 50 is positioned between the distal end of radius 20 and proximal row 18 of the carpal bones. A portion of radius 20 has been resected and implant 50 is positioned to receive or trap lunate bone 36. Implant 50 in effect replaces the radiocarpal joint.

Figure 7:
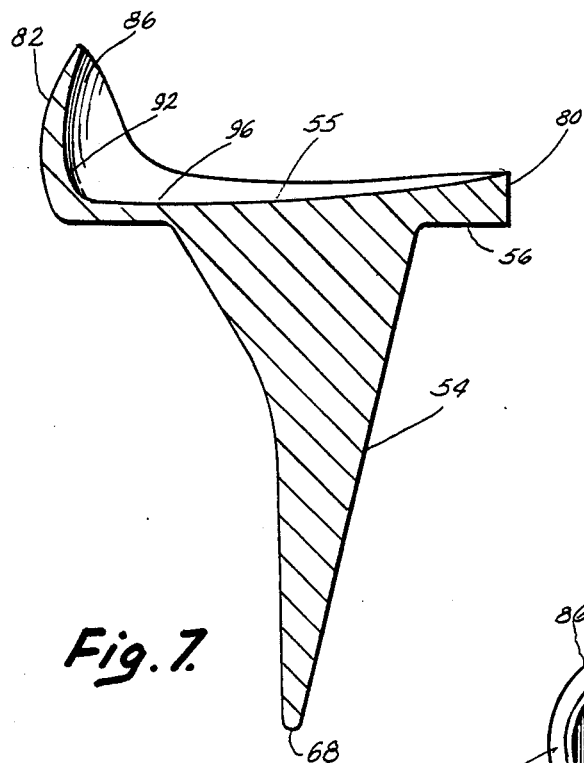
FIG. 7 is a cross-sectional view taken generally along line VII—VII of FIG. 5.
Figure 8:
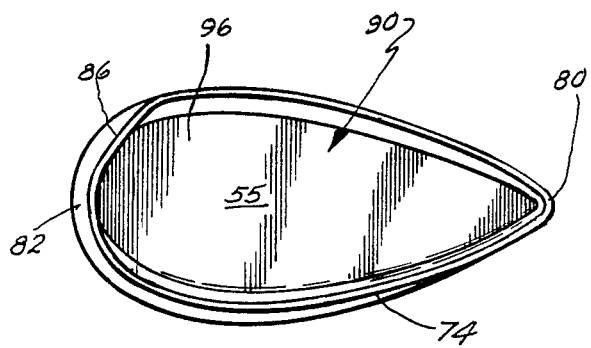
FIG. 8 is a view of the carpal surface of the implant.
Figure 9:
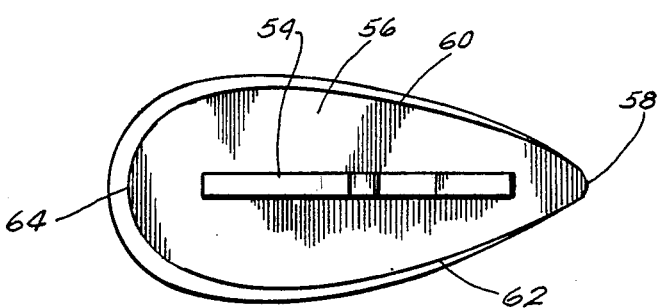
FIG. 9 is a view of the proximal surface or bottom of the implant.

As seen in FIGS. 3-9, implant 50 includes a body portion 52 and an intramedullary stem 54. Body portion 52 includes a base or bottom 55 which defines a proximal or bottom surface 56 (FIG. 9). Surface 56 has a generally teardrop shape and defines an apex 58, increasing radius, curved lateral or dorsal and palmar edges 60, 62, respectively, and a semicircular medial edge or base 64. Extending perpendicular to proximal surface 56 is intramedullary stem 54. Stem 54 extends from a point generally centrally of surface 56. Stem 54 is an elongated, planar member having a rectangular cross section. Stem 54 tapers from surface 56 to an apex or point 68. As shown in FIG. 2, stem 54 is dimensioned to extend into the intramedullary canal of radius 20.

Figure 4:
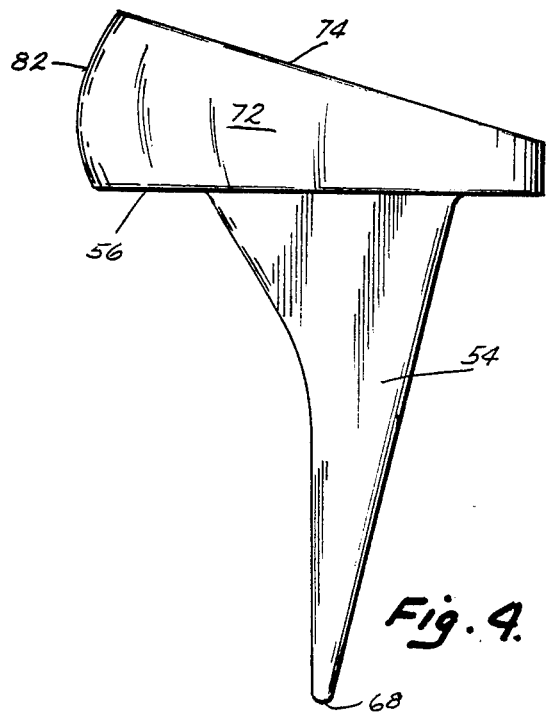
FIG. 4 is a dorsal view of the implant.
Figure 5:
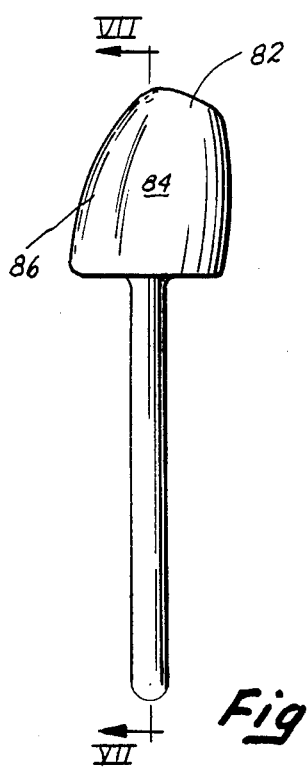
FIG. 5 is a medial end view of the implant.
Figure 6:
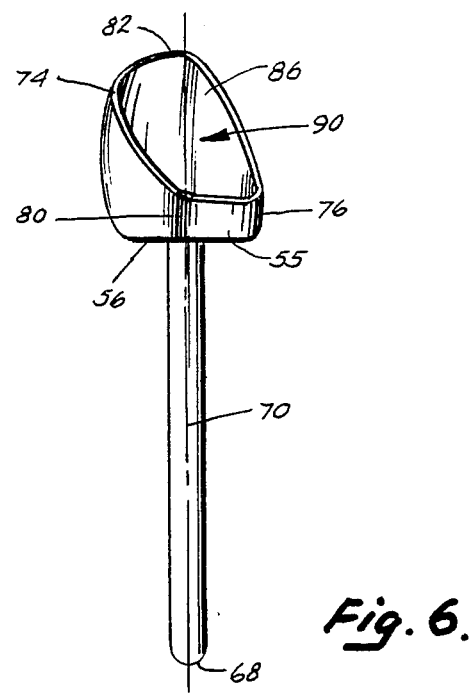
FIG. 6 is lateral end view of the implant.

Body portion 52 is nonsymmetrical about a plane 70 (FIG. 6). Body portion 52 includes a dorsal surface 72 defined by a sidewall 74 and a palmar surface 76 defined by base 55. Wall 74 tapers outwardly from an apex or lateral end 80. Wall 74 joins a medial end wall 82 having a surface 84. Surface 72, as seen in FIG. 4, is generally triangular or wedge-shaped in plan. End wall 82 is joined to base 55 by transition portion 86. The sidewall, end wall and base define a carpal recess 90. Recess 90 is generally L-shaped as viewed from the right side of FIG. 6 or in longitudinal cross section as shown in FIG. 7 including curved wall 74 and end or medial wall 82. Recess 90 tapers from medial wall 82 towards apex 80. Recess 90 is undercut at wall 82 to define a lunate surface 92. Recess 90 is configured so that lunate bone 36 is substantially disposed within the recess and partially encircled. Recess 90 is, however, open at its top at its end 80 and along one side. When in position, recess 90 opens distally and palmarly along a palmar edge 60 of base 55. The ulnar surface of the lunate abuts surface 92 of recess 90. Scaphoid 38 is also partially received within recess 90, as shown in FIG. 2. The proximal surfaces of the lunate and scaphoid bones will contact the curved base or bottom surface 96 of recess 90. Body portion 52 and the surfaces of recess 90 define a radiocarpal joint. Due to the configuration of the recess, the lunate bone and hence the proximal carpal row are in effect locked or constrained from moving medially toward the ulna 22. Dislocation of the carpal row is essentially prevented. Wrist movement does not, however, shift fully to the midcarpal joint. The open recess permits flexion and extension about surface 96. The proximal carpal row is not fully locked or restricted. The wrist is stabilized and the pain associated with ulnar displacement of the carpal row is reduced or substantially eliminated.

It is presently preferred that implant 50 be fabricated as a precision casting in a conventional fashion from titanium or a medical grade superalloy based on nickel and/or cobalt to which chromium is added for oxidation resistance. Such superalloys are well known in this industry. One such alloy is sold under the brand designation Vitallium. It is preferred that a plurality of implants of graduated size be provided to insure a stable fit with individual patients. Each of these implants would be graduated and have the same general proportions as the preferred embodiment illustrated. The principal concern is to provide a cup-shaped recess to constrain or restrict ulnar translation of the carpal bones. Also, should the head of the ulna be resected and a cap implant provided, implant 50 could provide a distal buttress and surface for the ulna head implant. As clearly seen in FIG. 2, with the implant in position and the ligamentous structures repaired, the proximal carpal row is held in its proper relationship to the distal end of the radius.

In an existing embodiment of the wrist implant in accordance with the present invention, body portion 52 has an overall longitudinal dimension "a" of approximately 1.30 inches and an overall width dimension "b" of approximately 0.625 inch, as indicated in FIG. 8. Medial surface 84 has an overall height "c" of approximately 0.475 inch, and apex 80 and base 55 have an overall height "d" of 0.150 inch, as indicated in FIG. 4. The distal edge of medial wall 82 has a radius "r" of approximately 0.20 inch, as shown in FIG. 8. Stem 54 has an overall length designated "e" in FIG. 4 of approximately 1.4 inches. Stem 54 has an overall transverse dimension designated "g" at the proximal surface 56 of approximately 0.70 inch. Stem 54 tapers to an overall transverse dimension designated "h" (FIG. 6) of approximately 0.30 inch at a distance "f" of approximately 0.50 inch from the proximal surface. Recess 90 has a highly polished or smooth finish and is cupped to conform generally to the exterior proximal, medial and dorsal surfaces of the lunate and scaphoid bones. Stem 54 has a thickness designated "t" (FIG. 6) of approximately 0.10 inch.

The wrist implant in accordance with the present invention is easily and relatively inexpensively manufactured using conventional fabrication techniques from suitable medical grade, high strength and wear resistant metals. A relatively simple surgical procedure may be employed to repair the wrist and prevent ulnar migration of the carpal row without significant loss of movement at the radiocarpal joint. This results in increased stability and freedom from pain.

The above description should be considered as that of the preferred embodiment. The true spirit and scope of the present invention may be determined by reference to the appended claims.

The embodiments of the invention in which an exclusive property or privilege is claimed are defined as follows:

1. A semi-constrained wrist implant for stabilizing the proximal carpal row and preventing ulnar migration of the carpal row while permitting adequate flexion and extension, said implant comprising:

a body having a generally wedge shape in dorsal plan view and being nonsymmetrical about a longitudinal plane, said body defining a generally triangular shaped proximal surface having a semicircular base and curved dorsal and palmar edges joining in a lateral apex, said body further defining a dorsal sidewall, an end wall joined to said dorsal sidewall and joined to said base through a transition portion and a slightly convex distal surface, said end wall, sidewall and distal surface defining a generally L-shaped, longitudinally extending recess which is open distally and palmarly, said sidewall and end wall defining a lunate surface within said recess, said recess dimensioned to receive and constrain the carpal row lunate and prevent ulnar migration of the row while providing adequate flexion of the radiocarpal joint.

2. A semi-constrained wrist implant as defined by claim 1 wherein said body is a one-piece member.

3. A semi-constrained wrist implant as defined by claim 2 wherein said body further includes an elongated intramedullary stem extending generally perpendicular from said proximal surface.

4. A semi-constrained wrist implant as defined by claim 3 wherein said body is formed from a medical grade metal.

5. A semi-constrained wrist implant as defined by claim 3 wherein said body is formed from titanium.

6. A semi-constrained wrist implant as defined by claim 3 wherein said body is formed from a superalloy.

* * * * *